US00PP34691P2

(12) United States Plant Patent
Van Dijk

(10) Patent No.: US PP34,691 P2
(45) Date of Patent: Oct. 25, 2022

(54) ***ANTHURIUM* PLANT NAMED 'AN2491496'**

(50) Latin Name: ***Anthurium andraeanum* L.**
Varietal Denomination: AN2491496

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/803,245

(22) Filed: Mar. 30, 2022

(51) Int. Cl.
*A01H 5/02* (2018.01)
*A01H 6/10* (2018.01)

(52) U.S. Cl.
USPC ..... Plt./366

(58) Field of Classification Search
USPC ..... Plt./365, 366
See application file for complete search history.

(56) References Cited

PUBLICATIONS

UPOV-PLUTO Plant Variety database; citation for 'AN2491496' (Retrieved from the Internet on May 24, 2022).*
EU Community Plant Variety Rights Application No. 2020/2998, Application n° A202003337, filed Nov. 26, 2020, 6 pages.
EU Community Plant Variety Office Official Gazette, 1.2021, Feb. 15, 2021, cover page, p. 31, and p. 52.

* cited by examiner

*Primary Examiner* — Susan McCormick Ewoldt
(74) *Attorney, Agent, or Firm* — Jondle & Associates, P.C.

(57) ABSTRACT

A new *Anthurium* plant named 'AN2491496' particularly distinguished by having large, medium blistered and medium glossy, concave, white, cordate, and durable spathes that retain the original color for a very long period of time with dark green, strongly concave, elliptical-cordate, durable leaves, white spadices with yellow tips, early and rich flowering continuously throughout the year, and a plant height of 35.0 cm to 40.0 cm is disclosed.

3 Drawing Sheets

Genus and species: *Anthurium andraeanum* L.
Variety denomination: 'AN2491496'.

BACKGROUND OF THE NEW PLANT

The present invention comprises a new and distinct variety of *Anthurium*, botanically known as *Anthurium andraeanum* L., and hereinafter referred to by the variety name 'AN2491496'. The new *Anthurium* plant is a product of a planned breeding program conducted by the inventor in Bleiswijk, the Netherlands. The objective of this breeding program was to create a new plant with a height of 35.0 cm to 40.0 cm having large, medium blistered and medium glossy, concave, white, cordate, and durable spathes.

The new variety originated from a cross-pollination made in March 2014 in Bleiswijk, the Netherlands. The female parent was a white *Anthurium* pot plant designated '24661-05' (unpatented), and the male parent was a white *Anthurium* pot plant designated '27904-04' (unpatented).

A single plant was selected from the progeny of the stated cross in December 2015. Asexual reproduction of the new variety by tissue culture in 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 26, 2020 (Application no. 2020/2998), by Applicant who obtained the subject matter disclosed directly from the inventor. 'AN2491496' has not been made publicly available or sold anywhere in the world prior to the effective filing date of this application with the exception of sales or disclosures made one year or less before the effective filing date of this claimed invention by Applicant who obtained 'AN2491496' directly from the inventor.

SUMMARY OF THE INVENTION

The following are the most outstanding and distinguishing characteristics of this new variety when grown under normal horticultural practices in Bleiswijk, the Netherlands:

1) Large, medium blistered and medium glossy, concave, white, cordate spathes;
2) White spadices with yellow tips;
3) Green, strongly concave, elliptical-cordate leaves; and
4) Spathes are positioned slightly above the leaves.

DESCRIPTION OF THE PHOTOGRAPHS

This new *Anthurium* plant is illustrated by the accompanying photographs which show the overall plant habit including blooms, bud, and foliage of the plant; the colors shown are as true as can be reasonably obtained by conventional photographic procedures. The photographs are of a 44-week-old plant grown in a greenhouse in Bleiswijk, the Netherlands, in February 2022. Colors in the photographs may differ from the color values cited in the detailed botanical description, which accurately describe the actual colors of the new variety.

DESCRIPTION OF THE NEW VARIETY

Figure 1:
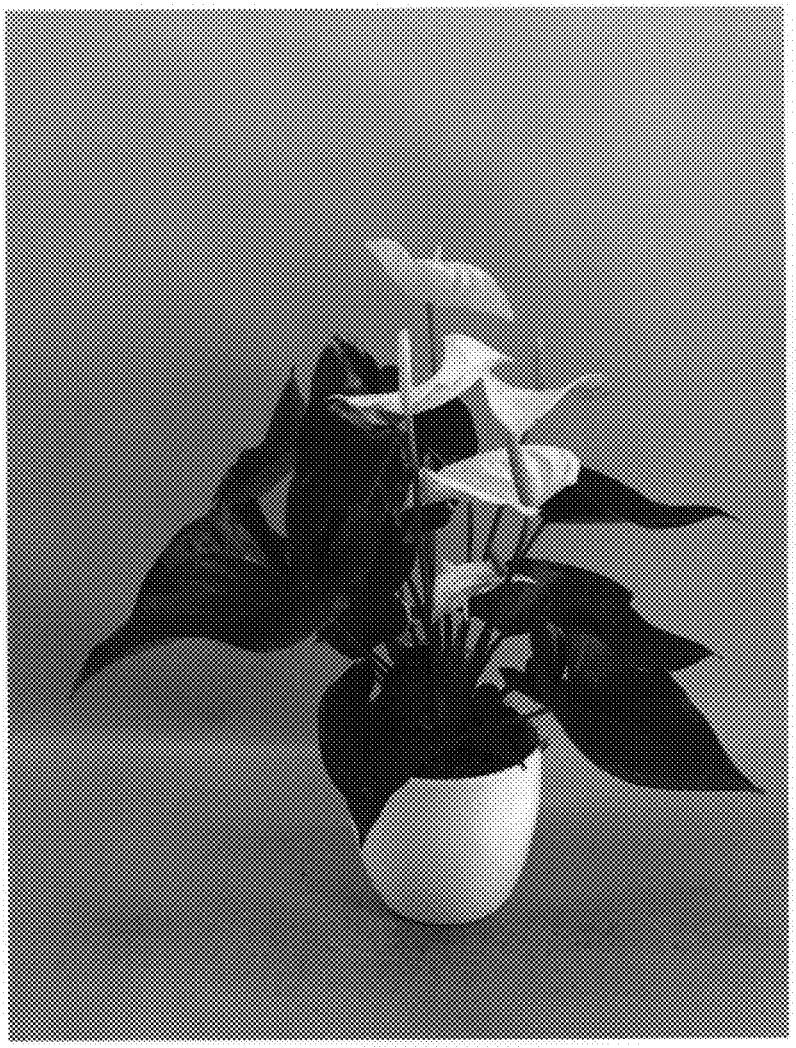
FIG. 1 shows the overall plant habit, including blooms, bud, and foliage.
Figure 2:
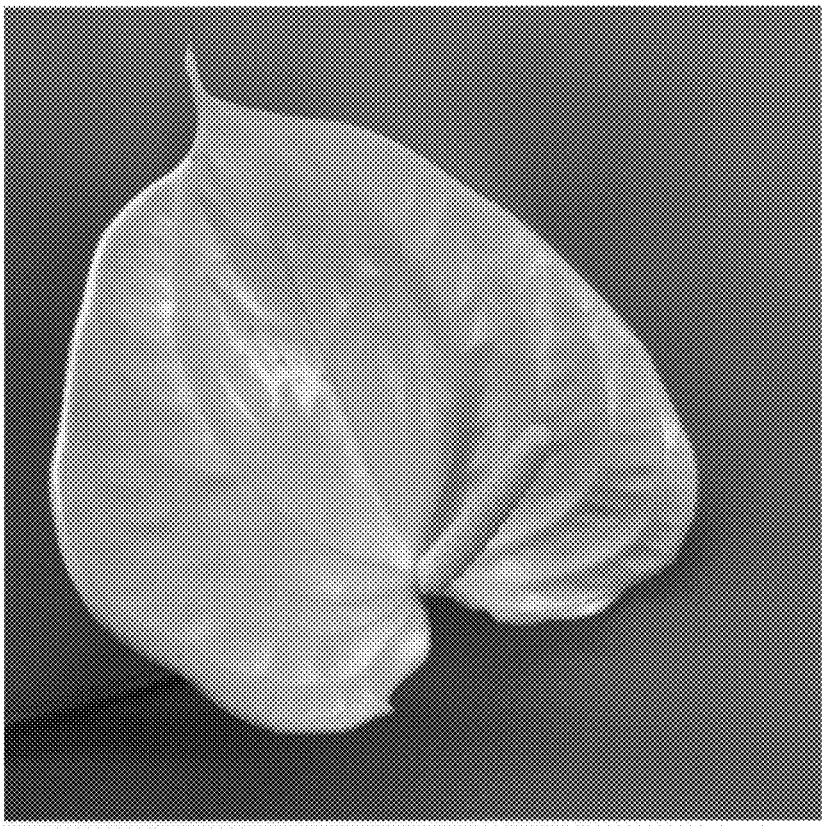
FIG. 2 shows a close-up of the mature spathe.
Figure 3:
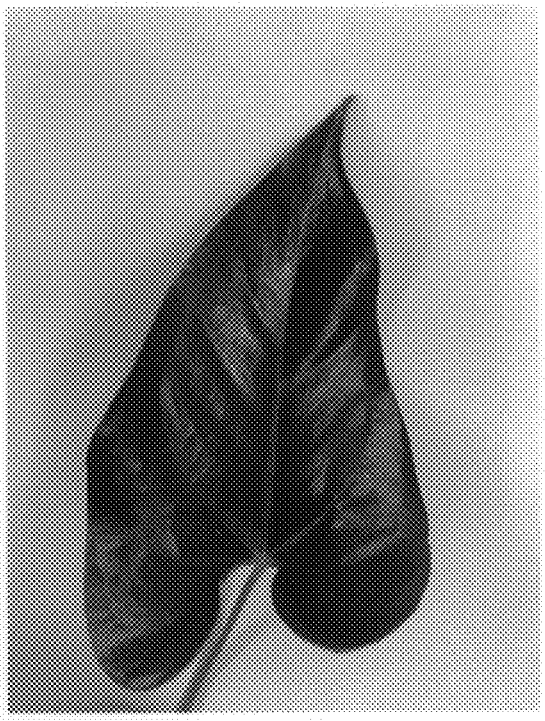
FIG. 3 shows a close-up of the upper leaf blade surface.
Figure 4:
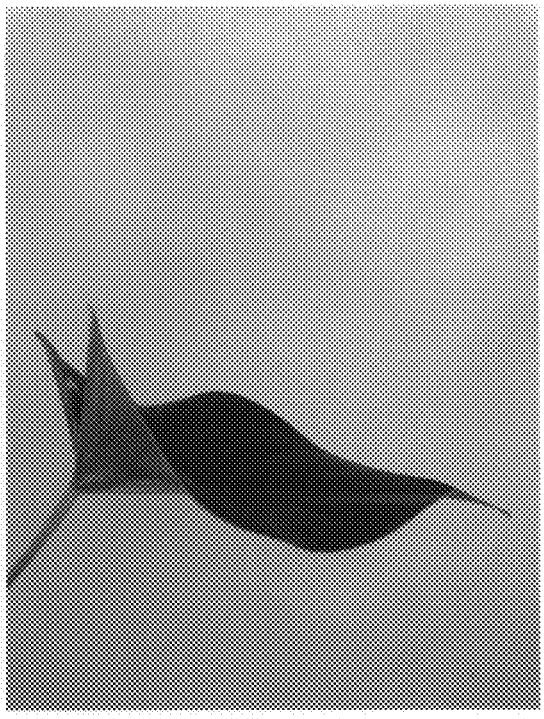
FIG. 4 shows a close-up of the leaf shape in cross section of middle zone.

The following detailed description sets forth the distinctive characteristics of 'AN2491496'. The data which define these characteristics were collected from asexual reproductions carried out in Bleiswijk, the Netherlands. The plant history was taken on 44-week-old plants which were planted from tissue culture in 14-centimeter (diameter) pots and grown in a glass greenhouse between 19° C. and 24° C. Observations were made in February 2022. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'AN2491496'.

Parentage:

*Female parent*.—*Anthurium* plant '24661-05' (unpatented).

*Male parent*.—*Anthurium* plant '27904-04' (unpatented).

Plant:

*Propagation*.—Tissue culture.

*Root description*.—Fleshy-creamy (RHS 160D) colored roots with small hairy lateral roots having yellow (RHS 9B) colored root tips.

*Time to produce a finished flowering plant*.—42 to 46 weeks after planting in a 14-cm (diameter) pot.

*Growth habit*.—Upright.

*Height* (*measured from soil, including inflorescence*).—35.0 cm to 40.0 cm.

*Width* (*measured from leaf tips*).—37.0 cm to 40.0 cm.

Leaves:

*Immature leaves*.—Length: 18.0 cm to 20.0 cm. Width: 10.0 cm to 12.0 cm. Color: Upper surface: RHS 146A. Lower surface: RHS 146B. Texture (both upper and lower surfaces): Glossy, leathery, and thin.

*Mature leaves*.—Length (fully expanded): 21.0 cm to 23.0 cm. Width: 12.0 cm to 14.0 cm. Shape: Elliptical cordate. Apex: Cuspidate. Base: Cordate. Leaf blade angle with the petiole: Between 110 degrees and 130 degrees. Leaf margin: Entire. Color: Upper surface: RHS 147A. Lower surface: RHS 146A. Texture: Upper surface: Leathery and thick. Lower surface: Glossy, leathery, and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes*.—Present. Arrangement: Leaf blade has two lobes extending past the petiole. The lobes are non-touching. Length of lobes of mature leaf blades: 4.0 cm to 5.0 cm. Width of lobes of mature leaf blades: 4.0 cm to 5.0 cm. Distance from petiole/leaf junction to highest point on lobes of mature leaf blades: 6.0 cm to 7.0 cm.

*Petiole*.—Cross-section: Round. Diameter: 0.4 cm to 0.5 cm. Length: 21.0 cm to 24.0 cm for a mature leaf size. Color: Mature leaf: RHS 144A. Immature leaf: RHS 144B. Cataphyll color surrounding the petiole: Outside: RHS 144B. Inside: RHS 144C.

*Geniculum*.—Length: 1.5 cm to 2.0 cm. Width: 0.4 cm to 0.5 cm. Color: RHS 144B.

Inflorescence:

*Arrangement*.—Single.

*Flowering habit* (*length of flowering season*).—Continuous.

*Number of inflorescences per plant*.—7 to 9.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully opened the peduncle elongates some extra centimeters.

*Arrangement*.—Spathe angle with the peduncle is between 90 degrees and 110 degrees; the spathe stands on a wiry peduncle about 3.0 cm to 6.0 cm above the foliage.

*Shape*.—Cordate.

*Apex*.—Abruptly acuminate.

*Base*.—Cordate.

*Texture*.—Medium blistered and medium glossy.

*Margin*.—Undulated.

*Size*.—Length: 13.0 cm to 14.0 cm. Width: 12.0 cm to 13.0 cm.

*Lobes*.—Present. Arrangement: The spathe has two lobes extending past the peduncle. The lobes are non-touching. Length: 1.0 cm to 1.5 cm. Width: 4.0 cm to 5.0 cm.

*Color*.—Just fully open: Upper surface: RHS NN155B. Lower surface: RHS NN155B. This white color remains for a very long period, at least more than 30 weeks after opening. The spathe turns green (RHS 144B and RHS 145B) after some weeks. Both colors are present.

Peduncle:

*Shape*.—Erect.

*Cross-section*.—Round.

*Length*.—28.0 cm to 31.0 cm.

*Diameter*.—0.4 cm to 0.6 cm.

*Color*.—RHS 144B.

Flowering time:

*General*.—One small, rooted, untreated tissue culture plant of 8.0 cm tall will flower, depending on the season, after 42 to 46 weeks and 7 to 8 blossoms appear. More blossoms appear after some additional weeks so that a full flowering and commercial plant will have 8 to 9 white spathes. Smaller blossoms may occur on immature plants.

Spadix:

*Size*.—Length: 4.5 cm to 5.0 cm (depending on flower size). Width (at apex): 0.5 cm to 0.6 cm. Width (at base): 0.6 cm to 0.7 cm.

*Shape*.—Columnar.

*Angle of spadix tip with peduncle*.—150 degrees to 160 degrees.

*Texture*.—When the spathe is unfurling, the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 13B. Mature: RHS 155B. Ages to: A color in between RHS 144A and RHS 144B.

Flowers:

*Quantity per spadix*.—180 to 210.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 155B.

Reproductive organs:

*Stamens*.—Not visible.

*Pollen amount*.—Absent.

*Pistil*.—Quantity: 180 to 210. Length: Less than 0.01 cm. Color: RHS 155B.

*Style*.—Not observed to date.

*Stigma*.—Shape: Ovoid. Diameter: Less than 0.01 cm. Color: RHS 155B.

*Ovary*.—Rarely visible.

*Ovary color*.—Not measured.

Fruit and seed set: None observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'AN2491496' differs from the female parent plant '24661-05' (unpatented) in that 'AN2491496' has cordate spathes that are concave in cross section of middle zone, whereas '24661-05' has orbicular-cordate spathes that are straight in cross section of middle zone. Additionally, 'AN2491496' has wider spathes than '24661-05'.

'AN2491496' differs from the male parent plant '27904-04' (unpatented) in that 'AN2491496' has strongly concave leaves and spathes that are concave in cross section of middle zone, whereas '27904-04' has weakly concave leaves and spathes that are straight in cross section of middle zone.

'AN2491496' differs from similar commercial variety 'ANTHDOZAJ' (U.S. Plant Pat. No. 27,730) in that 'AN2491496' has elliptical-cordate leaves, abruptly acuminate spathe apexes, and an angle of the spadix tip with the peduncle of 150 degrees to 160 degrees, whereas 'ANTHDOZAJ' has ovate leaves, broad acuminate spathe apexes, and an angle of the spadix tip with the peduncle of 170 degrees to 180 degrees.

'AN2491496' differs from similar variety 'ANTHERZEK' (U.S. Plant Pat. No. 28,327) in that 'AN2491496' has leaves that are strongly concave in cross section of middle zone and an angle of the spadix tip with the peduncle of 150 degrees to 160 degrees, whereas 'ANTHERZEK' has leaves that are medium concave in cross section of middle zone and an angle of the spadix tip with the peduncle of 165 degrees to 180 degrees. Additionally, 'AN2491496' has shorter spathe lobes than 'ANTHERZEK'.

I claim:

1. A new and distinct variety of *Anthurium* plant named 'AN2491496', substantially as illustrated and described herein.

* * * * *